United States Patent [19]

Arai et al.

[11] 3,990,896

[45] Nov. 9, 1976

[54] COLOR PHOTOGRAPHIC LIGHT SENSITIVE ELEMENT AND METHOD OF FORMING COLOR PHOTOGRAPHIC IMAGES

[75] Inventors: Atsuaki Arai; Akio Okumura; Seiji Ichijima; Keisuke Shiba; Kiyoshi Nakazyo, all of Minami-ashigara, Japan

[73] Assignee: Fuji Photo Film Co., Ltd., Minami-ashigara, Japan

[22] Filed: Oct. 9, 1974

[21] Appl. No.: 513,441

[30] Foreign Application Priority Data

Oct. 9, 1973  Japan.............................. 48-113634

[52] U.S. Cl.................................... 96/56.5; 96/74; 96/100; 96/56.2; 260/309.5
[51] Int. Cl.$^2$...................... G03C 7/00; G03C 1/40
[58] Field of Search ............. 96/100, 55, 56.2, 56.5

[56] References Cited
FOREIGN PATENTS OR APPLICATIONS 2,169,879   9/1973   France................................ 96/100

*Primary Examiner*—J. Travis Brown
*Attorney, Agent, or Firm*—Sughrue, Rothwell, Mion, Zinn & Macpeak

[57] ABSTRACT

A method of forming color photographic images which comprises developing an image-exposed photographic silver halide emulsion layer with a primary aromatic amino color developing agent in the presence of a yellow color forming coupler, in which one hydrogen atom of an active methylene group is substituted with a 5-alkylidene-3-hydantoinyl group and a color photographic light-sensitive element which comprises a silver halide emulsion containing a yellow color forming coupler, in which one hydrogen atom of an active methylene group of the coupler is substituted with a 5-alkylidene-3-hydantoinyl group. These yellow color forming couplers have a high coupling reactivity and additionally provide a stable coupler dispersion.

27 Claims, No Drawings

COLOR PHOTOGRAPHIC LIGHT SENSITIVE ELEMENT AND METHOD OF FORMING COLOR PHOTOGRAPHIC IMAGES

BACKGROUND OF THE INVENTION

1. Field of the Invention

The present invention relates to a method of forming color photographic images, and more particularly to a method of forming color photographic images using a novel yellow color forming coupler. The present invention also relates to a color photographic light sensitive element containing the novel yellow color forming coupler.

2. Description of the Prior Art

It is well known that color forming couplers couple with oxidation products of primary aromatic amino developing agents to form color photographic images. Most conventional yellow color forming couplers are four-equivalent couplers and these couplers require four moles of exposed silver halide as oxidizing agents to form one mole of azomethine dye. An introduction of a large amount of silver halide into light-sensitive layers leads to some disadvantages such as an increase in light scattering in the emulsion layers and consequently, a decrease in the sharpness of the images formed, and in addition, an increase in processing time for the light-sensitive materials due to an increase in thickness of the emulsion layers. Furthermore, the formation of dyes with these couplers is not completed during color development and thus it is necessary to use strong oxidizing agents in subsequent processing steps to complete the dye formation.

In order to improve these defects, two-equivalent yellow color forming couplers have been provided, which require only two moles of exposed silver halide to form one mole of azomethine dye.

The two-equivalent yellow color forming couplers have, in general, chemical structures in which one of the hydrogen atoms of the active methylene group is substituted with an atom or group releasable on coupling. Examples of such atoms or groups releasable on coupling are a fluorine atom as described in U.S. Pat. No. 3,277,155, a phenoxy group as described in U.S. Pat. No. 3,408,194, an acyloxy group as described in U.S. Pat. No. 3,447,928, a sulfoxy group as described in U.S. Pat. No. 3,415,652, and a group having a saccharin structure as described in German patent application Laid Open No. 2,057,941.

However, these couplers are not sufficient for use in color photography because they are accompanied by disadvantages in that the coupling reactivity is insufficient, in that a marked color fog is produced, in that the couplers per se are unstable and their coupling activities decrease or in that color stain occurs in the light-sensitive materials during storage, in that the yellow color images formed are unstable or in that the preparation of the couplers is quite difficult.

Couplers which improve these defects are yellow color forming couplers having a coupling releasable group derived from imide compounds as described in U.S. patent application Ser. Nos. 235,937, filed on Mar. 20, 1972 and 319,806, filed on Dec. 29, 1972 and Japanese patent application Laid Open No. 29432/73.

However, the couplers described in these patent specifications have an insufficient solubility in a coupler solvent and thus many difficulties are encountered in the manufacture of color photographic light-sensitive materials containing these couplers in that specific attention is required during preparation and storage of the coupler dispersion, in that the couplers crystallize in the coupler dispersion and they tend to promote uneven coating of emulsion layers resulting in a decrease in photographic properties of the layers. Therefore, development of two-equivalent yellow color forming couplers which have a good dispersion property and with which coating defects do not occur has been desired.

SUMMARY OF THE INVENTION

It is thus an object of the present invention to provide a two-equivalent yellow color forming coupler having good dispersibility and being free from coating difficulties which can be advantageously used in the production of photographic light-sensitive materials suitable for use in color photographic processes based on the subtractive process for color formation.

Another object of the present invention is to provide a method of forming dye images by developing a silver halide emulsion in the presence of a novel yellow color forming coupler.

Another object of the present invention is to provide a color photographic light-sensitive material which has a silver halide emulsion layer containing a novel yellow color forming coupler.

Another object of the present invention is to provide a color developer solution containing a novel yellow color forming coupler.

Still another object of the present invention is to provide a means for reducing the amount of silver halide contained in a photographic emulsion and improving the sharpness of images formed by the use of a novel yellow color forming coupler.

Still another object of the present invention is to provide a color photographic light-sensitive material which is well suited for use in rapid color developing processing in a blix bath containing both a weak oxidizing agent and a silver complex forming agent.

A further object of the present invention is to provide yellow color images which have spectral absorption characteristics suitable for the subtractive process for color formation and good stability.

A still further object of the present invention is to provide yellow color forming couplers suitable for use in the subtractive process for color formation.

A still further object of the present invention is to provide yellow color forming couplers which can form color images having a high sensitivity, a high gamma and a high density upon color development.

These and other objects of the present invention will become apparent from the following detailed description and examples as set forth below.

It has now been found that the above-described objects are accomplished with a yellow color forming coupler which has a 5-alkylidene-3-hydantoinyl group as a coupling releasable group.

Accordingly this invention provides a color photographic light sensitive element which comprises a silver halide emulsion containing a yellow color forming coupler, in which one hydrogen atom of an active methylene group of the coupler is substituted with a 5-alkylidene-3-hydantoinyl group. In another embodiment of this invention, this invention provides a method of forming color photographic images which comprises developing an image-exposed photographic silver halide emulsion layer with a primary aromatic amino color developing agent in the presence of a yellow color forming coupler, in which one hydrogen atom of an active methylene group of the coupler is substituted with a 5-alkylidene-3-hydantoinyl group.

DETAILED DESCRIPTION OF THE INVENTION

The open-chain ketomethylene type yellow color forming couplers which are used in the present invention can be characterized as couplers in which one of the hydrogen atoms of the active methylene group is substituted with a 5-alkylidene-3-hydantoinyl group and the 1-position of the hydantoinyl group can have a substituent such as an alkyl group, an aryl group, an acyl group or the like and the hydantoinyl group can be split off when the coupler reacts to couple with the oxidation product of a primary aromatic amino developing agent.

On the yellow color forming couplers which can be used in the present invention, the compounds represented by the following general formula (I) are useful.

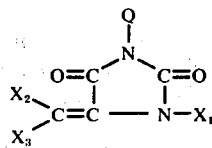
(I)

wherein $X_1$ represents a hydrogen atom, an alkyl group, an aryl group or an acyl group, or $X_1$ can combine with $X_2$ to form a 5-membered or a 6-membered ring; $X_2$ and $X_3$, which may be the same or different, each represents a hydrogen atom, an alkyl group or a halogen atom, or $X_2$ and $X_3$ can combine with each other to form a 5-membered or a 6-membered ring; Q represents a residue of an open-chain ketomethylene type yellow color forming coupler in which one hydrogen atom attached to the active methylene group of the coupler is eliminated.

In the general formula (I), the alkyl group represented by $X_1$, $X_2$ or $X_3$ can be in the form of a chain or a ring and an alkyl group having up to about 25 carbon atoms is suitable. The alkyl group can be a substituted alkyl group. Examples of such substituents are an aryl group, an alkoxy group, an aryloxy group, an alkoxycarbonyl group, an acylamino group, a carboxy group, a hydroxy group, a carbamoyl group, a sulfamoyl group, a cyano group, a halogen atom or the like. Suitable examples of alkyl groups are a methyl group, an ethyl group, a butyl group, a dodecyl group, a benzyl group, a carboxymethyl group, an ethoxymethyl group, an acetylaminomethyl group, a 2-cyanoethyl group, a hydroxymethyl group, an ethoxycarbonylmethyl group, a chloromethyl group, etc.

The aryl group represented by $X_1$ includes a phenyl group, a naphthyl group and the like, and these aryl groups can be substituted. Examples of such substituents are an alkyl group, an aryl group, an alkoxy group, an aryloxy group, an alkoxycarbonyl group, an acylamino group, a carboxy group, a hydroxy group, a carbamoyl group, a sulfamoyl group, a cyano group, a nitro group, a halogen atom, or the like. Suitable examples of aryl groups are a phenyl group, a naphthyl group, a 4-carboxyphenyl group, a 4-methoxyphenyl group, a 3-methylphenyl group, a 3-butoxycarbonylphenyl group, 3-N-ethylcarbamoylphenyl group, a 4-N,N-diethylsulfamoylphenyl group, a 3-nitrophenyl group, a 4-chlorophenyl group, a 4-hydroxyphenyl group, a 4-acetylaminophenyl group, etc.

As the acyl group represented by $X_1$, an acyl group having up to about 25 carbon atoms is suitable, such as, for example, acetyl, propionyl, stearoyl, benzoyl, or the like.

Suitable coupler residues represented by Q in the general formula (I) are coupler residues in which two carbonyl groups are attached directly to the active methylene group to which the 5-alkylidene-3-hydantoinyl group is connected. Representative examples of such coupler residues are derived from α-acylacetamides.

Particularly suitable yellow color forming couplers which can be used in the present invention are represented by the following general formula (II):

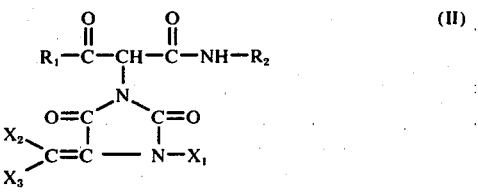

wherein $R_1$ represents an aliphatic group, an aromatic group or a heterocyclic group; $R_2$ represents an aromatic group or a heterocyclic group; and $X_1$, $X_2$ and $X_3$ each have the same meaning as defined in the general formula (I).

In the general formula (II), suitable aliphatic groups represented by $R_1$ include a substituted or unsubstituted alkyl group which can be in the form of a chain or can be a cyclic group. Suitable substituents on the alkyl group are an alkenyl group, an aryl group, an alkoxy group, an aryloxy group, an acyl group, an amino group, a carboxy group, an acylamino group, a carbamoyl group, an imido group, an alkoxycarbonyl group, an acyloxy group, a sulfo group, a sulfonyl group, a sulfonamido group, a sulfamoyl group, etc., and which in turn can be further substituted. Suitable specific examples of aliphatic groups for $R_1$ are as follows: methyl, ethyl, propyl, isopropyl, butyl, isobutyl, tert-butyl, amyl, isoamyl, tert-amyl, hexyl, 1-methylpentyl, 2-methylpentyl, neopentyl, 1,1-dimethylbutyl, heptyl, 1-methylhexyl, 2-methylhexyl, 3-methylhexyl, 5-methylhexyl, 1,1-dimethylhexyl, octyl, 2-ethylhexyl, 1,1-diethylhexyl, nonyl, isononyl, decyl, undecyl, dodecyl, tetradecyl, hexadecyl, octadecyl, 1,1-dimethylnonyldecyl, 1,1-diamylhexyl, 1-methyl-1-nonyldecyl, cyclopropyl, cyclobutyl, cyclopentyl, cyclohexyl, benzyl, phenethyl, allyl, oleyl, 7,7-dimethylnorbornyl, 1-methylcyclohexyl, 2-methoxyisopropyl, 2-benzylisopropyl, 2-phenoxyisopropyl, 2-p-tert-butylphenoxyisopropyl, 2-naphthoxyisopropyl, cinnamyl, α-aminoisopropyl, α-(N,N-diethylamino)isopropyl, α-(succinimido)isopropyl, α-(phthalimido)isopropyl, α-(benzenesulfonamido)isopropyl, etc.

The aromatic groups represented by $R_1$ and $R_2$ include a substituted or unsubstituted phenyl group. Suitable substituents can be monovalent substituents such as a halogen atom, a nitro group, a cyano group, a thiocyano group, a hydroxy group, an alkoxy group, an aryloxy group, an acyloxy group, an alkyl group, an alkenyl group, an aryl group, an amino group, a carboxy group, an acyl group, an alkoxycarbonyl group, an aryloxycarbonyl group, a carbamoyl group, an acylamino group, an imido group, a sulfo group, an alkylsulfonyl group, an arylsulfonyl group, an alkoxysulfonyl group, an aryloxysulfonyl group, a sulfamoyl group, a sulfonamido group, an ureido group, a thioureido group, etc., and further divalent substituents which can form a condensed ring together with the phenyl group. Examples of phenyl groups having such a divalent substituent are a naphthyl group, a quinolyl group, an isoquinolyl group, a chromanyl group, a coumaranyl group, a tetrahydronaphthyl group, etc. These monovalent and divalent substituents can, in turn, have further substituents. In particular $R_1$ can be a phenyl group or phenyl group substituted with an electron donating group.

The heterocyclic groups represented by $R_1$ and $R_2$ are connected through a carbon atom which forms the heterocyclic ring to the carbon atom of the carbonyl group of the acyl group and the nitrogen atom of the amido group in the α-acylacetamide, respectively. Such heterocyclic groups include those of the thiophane series (for example, 2-thienyl, 3-thienyl, 2-benzothienyl, 3-benzothienyl, 2-naphthothienyl, 3-naphthothienyl, etc. the furan series (for example, 2-furyl, 3-furyl, 2-benzofuranyl, 3-benzofuranyl, 1-isobenzofuranyl, 3-isobenzofuranyl, etc.), the pyran series (for example, 3-pyranyl, 4-pyranyl, 5-pyranyl, 6-pyranyl, etc.), the chromene series (for example, 3-chromenyl, 4-chromenyl, etc.), the pyrrole series (for example, 2-pyrrolyl, 1-methyl-3-pyrrolyl, etc.), the pyrazole series (for example, 4-pyrazolyl, 1-phenyl-3-pyrazolyl, etc.), the pyridine series (for example, 2-pyridyl, 3-pyridyl, 4-pyridyl, 2-quinolyl, 3-quinolyl, 4-quinolyl, 1-isoquinolyl, 3-isoquinolyl, 4-isoquinolyl, etc.), the pyrazine series (for example, 2-pyrazinyl, 2-quinoxalinyl, etc.), the pyrimidine series (for example, 2-pyrimidinyl, 4-pyrimidinyl, 5-pyrimidinyl, 2-quinazolinyl, 4-quinazolinyl, etc.), the pyridazine series (for example, 2pyridazinyl, 3-pyridazinyl, 3-cinnolinyl, 4-cinnolinyl, etc.), the indolizine series (for example, 1-indolizinyl, 2-indolizinyl, 3-indolizinyl, 5-indolizinyl, 6-indolizinyl, 7-indolizinyl, etc.) the perimidine series (for example, 2-perimidinyl, etc.), the thiazole series (for example, 2-thiazolyl, 2-benzothiazolyl, 3-isothiazolyl, 4-isothiazolyl, 5-isothiazolyl, etc.), the imidazole series (for example, 2-benzoimidazolyl, etc.), the oxazole series (for example, 2-oxazolyl, 4-oxazolyl, etc.), the 1,3,5-triazine series (for example, 1,3,5-triazinyl, etc.), the oxazine series (for example, 2-oxazinyl, 4-oxazinyl, etc.), etc. These heterocyclic groups can be substituted with a halogen atom (such as chlorine, bromine, etc.), a nitro group, a cyano group, a thiocyano group, a hydroxy group, an alkoxy group, an aryloxy group, an acyloxy group, an alkyl group, an alkenyl group, an aryl group, an amino group, a carboxy group, an acyl group, an alkoxycarbonyl group, an aryloxycarbonyl group, a carbamoyl group, an acylamino group, an imido group, a sulfo group, an alkylsulfonyl group, an arylsulfonyl group, an alkoxysulfonyl group, an aryloxysulfonyl, a sulfamoyl, a sulfonamido group, an ureido group, a thioureido group, etc.

It should be understood that the yellow color forming couplers represented by the general formula (II) which can be used in the present invention include compounds in which two coupler residues are bonded to each other through $R_1$ or $R_2$ as a divalent group of the monovalent groups previously described for $R_1$ or $R_2$ in the general formula (II). In such case, the yellow color forming couplers can have the following structures:

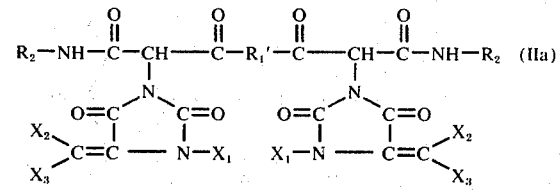

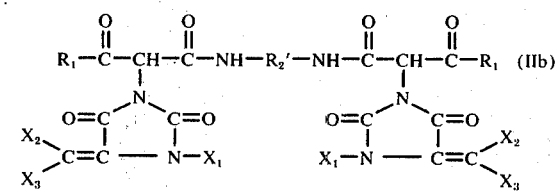

in which $R_1$, $R_2$, $X_1$, $X_2$ and $X_3$ are the same as defined in the general formula (II), $R_1'$ and $R_2'$ each represents a divalent group corresponding to $R_1$ or $R_2$, respectively, in the general formula (II).

Yellow color forming couplers in which $R_1$ in the abovedescribed general formula (II) is an alkyl group in which a tertiary carbon atom is bonded to the carboxyl group, particularly, a tert-butyl group, are preferred. Also, yellow color forming couplers in which $R_1$ is a phenyl group or a phenyl group substituted with an electron-donating group such as an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an amino group (for example, amino, N,N-dimethylamino, N-butyl-N-octylamino, etc.) are preferred.

Yellow color forming couplers in which $R_2$ in the abovedescribed general formula (II) is a phenyl group in which one of the ortho positions is substituted with a halogen atom (for example, fluorine, chlorine, bromine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino etc.) are preferred.

Of these yellow color forming couplers which can be used in the present invention, the compounds represented by the following general formulae (III) and (IV) are particularly preferred.

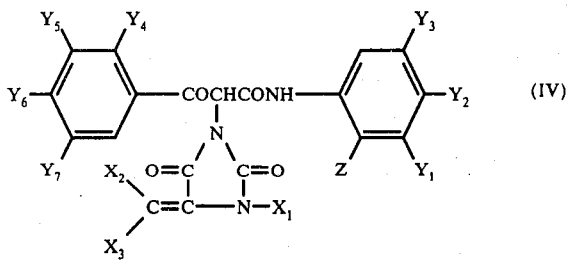

in which $X_1$, $X_2$ and $X_3$ are the same as defined in the general formula (I), and Z represents a halogen atom (for example, fluorine, chlorine, bromine, etc.), an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), or an N-substituted amino group (for example, N,N-dimethylamino, N-butyl-N-octylamino etc.), $Y_1$, $Y_2$ and $Y_3$, which may be the same or different, each represents a hydrogen atom, a halogen atom (for example, fluorine, chlorine, bromine, etc.), an alkyl group (for example, methyl, ethyl, allyl, octadecyl, etc.), an alkoxy group (for example, methoxy, ethoxy, dodecyloxy, etc.), an aryl group (for example, phenyl, methylphenyl, etc.), an aryloxy group (for example, phenoxy, methylphenoxy, etc.), an alkoxycarbonyl group (for example, methoxycarbonyl, hexadecyloxycarbonyl, etc.), a carbamoyl group (for example, methylcarbamoyl, dodecylcarbamoyl, etc.), a sulfamoyl group (for example, methylsulfamoyl, diethylsulfamoyl, N-γ-(2,4-di-tert-amylphenoxy)propylsulfamoyl, etc.), an alkylamino group (for example, ethylamino N,N-dimethylamino, etc.), arylamino group (for example, anilino, etc.), an acylamino group (for example, acetamido, α-(3-pentadecylphenoxy)butyramido, etc.), a carboxy group, a sulfo group, a cyano group or a hydroxy group, $Y_4$, $Y_5$, $Y_6$ and $Y_7$, which may be the same or different, each represents a hydrogen atom, an alkyl group (for example, methyl, ethyl, tert-butyl, etc.), an alkoxy group (for example, methoxy, ethoxy, propoxy, octoxy, etc.), an aryloxy group (for example, phenoxy, methylphenoxy, etc.), an amino group (for example, an amino, N,N-dimethylamino, N-butyl-N-octylamino, etc.), or an acylamino group (for example, acetamido, α-(2,4-di-tert-amylphenoxy)butyramido, etc.).

Representative examples of yellow color forming couplers which can be used in the present invention are illustrated below.

1. α-(4-Methoxybenzoyl)-α-(5-isopropylidene-3-hydantoinyl)-2'-chloro-5'-tetradecyloxycarbonylacetanilide
2. α-{3-[α-(2,4-Di-tert-amylphenoxy)butyramido]benzoyl}-α-(5-isopropylidene-3-hydantoinyl)-2'-methoxyacetanilide
3. α-(4-Methoxybenzoyl)-α-(5-α-bromo-n-propylidene-3-hydantoinyl)-2'-chloro-5'-[α-(2,4-di-tert-amylphenoxy)butyramido]acetanilide
4. α-Benzoyl-α-(5-α-bromo-n-propylidine-3-hydantoinyl)-2'-methoxy-5'-dodecyloxycarbonylacetanilide
5. α-(4-Methoxybenzoyl)-α-(5-α-bromo-n-propylidene-3-hydantoinyl)-2'-chloro-5'-[γ-(2,4-di-tert-amylphenoxy)butyramido]acetanilide
6. α-{3-[α-(2,4-Di-tert-amylphenoxy)butyramido]-4-methoxybenzoyl}-5-(5-α-bromoethylidene-3-hydantoinyl)-2'-methoxy-5'-N,N-diethylsulfamoylacetanilide
7. α-(2-Furoyl)-α-(5-isopropylidene-1-phenyl-3-hydantoinyl)-2'-chloro-5'-[α-(2,4-di-tert-amylphenoxy)butyramido]acetanilide
8. α-(4-Methoxybenzoyl)-α-(5-α-bromo-n-propylidene-3-hydantoinyl)-2'-methoxy-5'-tetradecyloxycarbonylacetanilide
9. α-Pivaloyl-α-(5-isopropylidene-3-hydantoinyl)-2'-chloro-5'-[γ-(2,4-di-tert-amylphenoxy)butyramido]acetanilide
10. α-Pivaloyl-α-(5-isopropylidene-3-hydantoinyl)-2'-chloro-5'-[α-(2,4-di-tert-amylphenoxy)butyramido]acetanilide
11. α-(4-Methoxybenzoyl)-α-(5-isopropylidene-3-hydantoinyl)-2'-chloro-5'-[γ-(2,4-di-tert-amylphenoxy)butyraido]acetanilide
12. α-Pivaloyl-α-(5-methylene-3-hydantoinyl)-2'-chloro-5'-[γ-(2,4-di-tert-amylphenoxy)butyramido]acetanilide
13. α-(4-Methoxybenzoyl)-α-(5-cyclohexylidene-3-hydantoinyl)-2'-chloro-5'-[α-(2,4-di-tert-amylphenoxy)butyramido]acetanilide
14. α-(4-Methoxybenzoyl)-α-(1-methyl-5-methylene-3-hydantoinyl)-2'-chloro-5'-tetradecyloxycarbonylacetanilide
15. α-Pivaloyl-α-(1,3-dioxo-1H-pyrrolo[1,2-c]imidazolidin-2-yl)-2'-chloro-5'-[α-(2,4-di-tert-amylphenoxy)butyramido]acetanilide
16. α-(2-Methylbenzoyl)-α-(5-cyclohexylidene-3-hydantoinyl)-2'-chloro-5'-dodecyloxycarbonylacetanilide
17. α-Pivaloyl-α-(5-α-bromo-n-propylidene-3-hydantoinyl)-2'-methoxy-5'-hexadecyloxycarbonylacetanilide
18. α-Pivaloyl-α-(5-isopropylidene-3-hydantoinyl)-2'-methoxy-5'-(N-γ-2,4-di-tert-amylphenoxypropylsulfamoyl)acetanilide
19. α-(2-Methylbenzoyl)-α-(1-acetyl-5-isopropylidene-3-hydantoinyl)-2'-methoxy-5'-tetradecyloxycarbonylacetanilide
20. α-Benzoyl-α-(5-isopropylidene-3-hydantoinyl)-2'-methoxyacetanilide
21. α-Pivaloyl-α-(5-α-bromo-n-propylidene-3-hydantoinyl)-2',4'-dichloroacetanilide The yellow color forming couplers of the present invention can generally be prepared by reacting a halogenated compound in which one hydrogen atom attached to the active methylene group of a 4-equivalent coupler residue is substituted with a halogen atom, preferably a chlorine atom or a bromine atom, with a salt, preferably the potassium salt, of an imide to be reacted, in an organic solvent. Specific examples of 4-equivalent yellow color-forming couplers are described in, for example, U.S. Pat. Nos. 2,875,057; 3,265,506; 3,277,155; 3,408,194; 3,409,439; 3,415,652; 3,447,928; 3,551,155; 3,551,156; 3,582,322; 3,685,995; etc. The halogenated compound which can be used in the preparation of the yellow color forming couplers of the present invention can be prepared by the method as described in U.S. Pat. Nos. 2,728,658 and 3,447,928. The imide which can be used in the preparation of the yellow color forming couplers of the present invention can be prepared by the method as described in *J. Am. Chem. Soc.*, Vol. 76, page 5636 (1954). The halogenated 4-equivalent coupler residue can be generally used in a molar ratio of from about 1 to about 5 moles, preferably 2 to 3 moles, per mole of the imide salt. Examples of organic solvents which can be used in this invention are alcohols such as methanol, ethanol, isopropanol, etc., halogenated hydrocarbons such as chloroform, methylchloroform, etc., hydrocarbons such as ligroin, hexane, etc., aromatic hydrocarbons such as benzene, toluene, xylene, etc., amides such as dimethylformamide, diethylacetamide, hexamethylphosphoramide, N-methyl-2-pyrolidone, tetramethylurea, etc., sulfoxides such as dimethylsulfoxide, etc., acetonitrile, or the like, preferably dimethylformamide, dimethylsulfoxide, at room temperature (about 20°–30° C). Although the reaction between the halogenated compound and the imide can be effected in various manners, it can be advantageously carried out by dissolving each of the reactants separately in a solvent illustrated above and combining the solutions. A suitable concentration of the reactant in each solution is in the range of from about 2 to about 50% by weight, preferably 5 to 20% by weight. The preparation of the yellow color forming couplers is illustrated in greater detail by the following synthesis examples. Unless otherwise indicated herein, all parts, percents, ratios and the like are by weight.

SYNTHESIS EXAMPLE 1

Preparation of
α-Pivaloyl-α-(5-α-bromo-n-propylidene-3-hydantoinyl)-2'-chloro-5'-[α-(2,4-di-tert-amylphenoxy)-butyramido]acetanilide To a solution containing 4 g of potassium hydroxide dissolved in 15 ml of methanol, was added a solution containing 17 g of 5-α-bromo-n-propylidenehydantoin dissolved in 50 ml of dimethylformamide, and further was added dropwise a solution containing 25 g of α-pivaloyl-α-chloro-2'-chloro-5'-[α-(2,4-di-tert-amylphenoxy)butyramido]acetanilide dissolved in 250 ml of dimethylformamide. After being stirred for 2 hours at room temperature, the reaction mixture was poured into 2 liters of water, and extracted with 1 liter of ethyl acetate. The ethyl acetate layer was separated, washed with a dilute hydrochloric acid solution, washed with water and dried over anhydrous sodium sulfate. The ethyl acetate was distilled off under reduced pressure, and the residue was recrystallized from a solvent mixture of n-hexane and ethyl acetate, yielding 18 g of the coupler. The melting point was 129° to 131° C.

SYNTHESIS EXAMPLE 2

Preparation of
α-Pivaloyl-α-(5-isopropylidene-3-hydantoinyl)-2'-chloro-5'-[α-(2,4-di-tert-amylphenoxy)-butyramido]acetanilide The same procedure as described in Synthesis Example 1 were carried out except for the use of 5-isopropylidenehydantoin in place of the 5-α-bromo-n-propylidenehydantoin to give the coupler. The melting point was 178° to 179° C.

SYNTHESIS EXAMPLE 3

Preparation of
α-(4-Methoxybenzoyl)-α-(5-α-bromo-n-propylidene-3-hydantoinyl)-2'-chloro-5'-[α-(2,4-di-tert-amylphenoxy)butyramido]acetanilide The same procedures as described in Synthesis Example 1 were carried out except for the use of α-(4-methoxybenzoyl)-α-bromo-2'-chloro-5'-[α-(2,4-di-tert-amylphenoxy)butyramido]acetanilide in place of the α-pivaloyl-α-chloro-2'-chloro-5'-[α-(2,4-di-tert-amylphenoxy)butyramido]acetanilide. The product was recrystallized from methanol to give the coupler. The melting point was 112° to 113.5° C.

SYNTHESIS EXAMPLE 4

Preparation of
α-(4-Methoxybenzoyl)-α-(5-isopropylidene-3-hydantoinyl)-2'-chloro-5'-[γ-(2,4-di-tert-amylphenoxy)-butyramido]acetanilide The same procedures as described in Synthesis Example 2 were carried out except for the use of α-(4-methoxybenzoyl)-α-bromo-2'-chloro-5'-[γ-(2,4-di-tert-amylphenoxy)butyramido]acetanilide in place of the α-pivaloyl-α-chloro-2'-chloro-5'-[α-2,4-di-tert-amylphenoxy)butyramido]acetanilide to give the coupler. The melting point was 140° to 141° C.

Methods of forming yellow color images according to the present invention include an embodiment in which the yellow color forming couplers are present in a photographic emulsion layer, and an embodiment in which the yellow color forming couplers are present in a color developer solution. The former is designated a coupler-in-the-emulsion type, and in which the couplers are usually incorporated in an emulsion layer during the manufacture of photographic light-sensitive materials. The latter is designated a coupler-in-the-developer type, and in which the couplers are usually dissolved in a color developer solution and diffuse into an emulsion layer during the color development.

Couplers which can be used in the coupler-in-the-emulsion type are desired to be fixed in a specific emulsion layer. That is, these must be diffusion resistant. Otherwise these couplers migrate in a photographic light-sensitive material and form dyes in other emulsion layers of different spectral sensitivity resulting in a marked reduction in the color reproducibility of the photographic materials.

In order to render the couplers diffusion resistant, it is preferred to introduce a group containing a hydrophobic group having about 8 to about 32 carbon atoms into the coupler molecule. Such groups are conventionally designated ballasting groups and various kinds of ballasting groups are well known in the art. The ballasting group can be connected to the coupler skeleton either directly or through an amino bond, an ether bond, a thioether bond, a carbonamido bond, a sulfonamido bond, an ureido bond, an ester bond, an imido bond, a carbonyl bond, a sulfonyl bond, or the like.

In the yellow color forming couplers which can be used in the present invention, any of the known ballasting groups can be used. In the yellow color forming couplers represented by the above-described general formula (II), such a group can be introduced into at least one of $R_1$ and $R_2$.

Specific examples of the ballasting groups are illustrated below.

i. Alkyl and alkenyl groups:
For example,

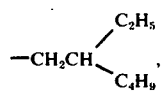

$—C_{12}H_{25}$, $—C_{16}H_{33}$, or $—C_{17}H_{33}$ ii. Alkoxyalkyl groups:
For example,

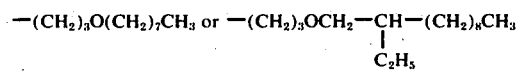

as described in Japanese Patent Publication No. 27563/64 iii. Alkylaryl groups:
For example

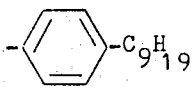

or

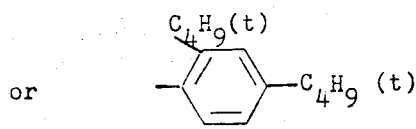

iv. Alkylaryloxyalkyl groups:
For example,

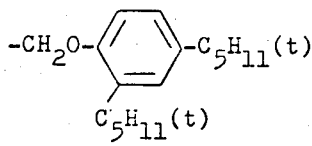

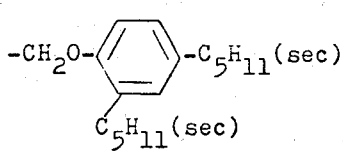

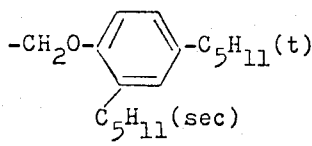

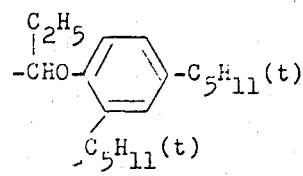

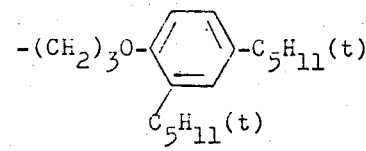

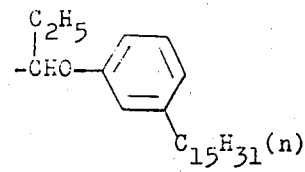

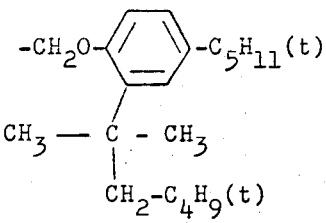

or

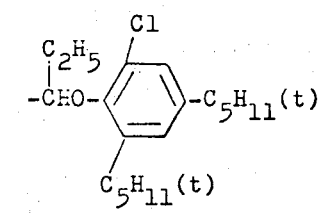

v. Acylamidoalkyl groups:
For example,

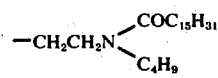

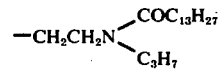

or

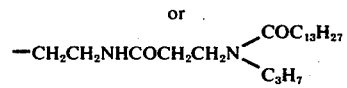

as described in U.S. Pat. Nos. 3,337,344 and 3,418,129.

vi. Alkoxyaryl and aryloxyaryl groups:
For example,

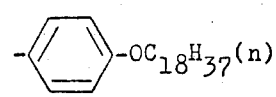

or

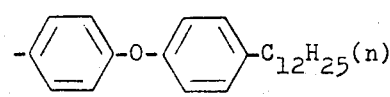

vii. Residual groups containing a long chain aliphatic group, such as alkyl or an alkenyl group, together with a water-solubilizing group such as a carboxy or a sulfo group:
For example,

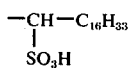

or

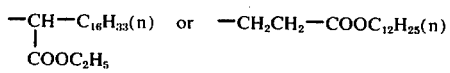

viii. Ester substituted alkyl groups:
For example, ix. Aryl or heterocyclic group substituted alkyl groups:
For example,

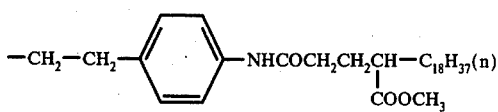

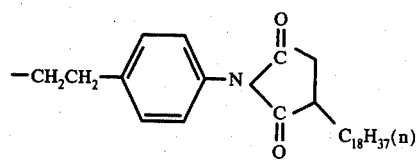

x. Aryloxyalkoxycarbonyl substituted aryl groups:
For example,

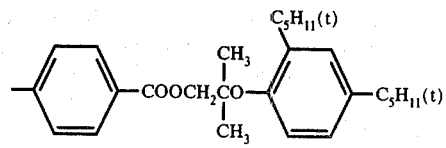

A coupler having diffusion resistant group in the molecule can be dissolved in an organic solvent and incorporated into a photographic emulsion as fine particles in a conventional manner. An example of a method of dispersing the couplers which is particularly suitable in the practice of the present invention is described in detail in U.S. Pat. No. 3,676,131. Organic solvents which are used to dissolve the coupler include those solvents which are sparingly soluble in water and have a high boiling point (higher than 170° C) and remain in a color photographic light-sensitive material together with the couplers, for example, hydrocarbons, carboxylic acid esters, carboxylic acid amides, phosphoric acid esters, ethers, and the like. Specific examples of these solvents are di-n-butyl phthalate, di-isooctyl azelate, di-n-butyl sebacate, tricresyl phosphate, tri-n-hexyl phosphate, N,N-diethylcaprylamide, butyl-m-pentadecylphenylether, p-n-nonylphenol, 2-methyl-4-n-octylphenol, acetyl tri-butyl citrate, tributyl glyceride, and the like. An auxiliary solvent which can be removed during the production of the photographic light-sensitive material is advantageously used in combination with the high boiling solvent to facilitate the dissolution of the coupler. Examples of such solvents are propylene carbonate, ethyl acetate, butyl acetate, cyclohexanol, tetrahydrofuran, cyclohexanone, and the like.

To facilitate the formation of a fine dispersion of the oil-soluble incorporated type couplers into a hydrophilic high molecular weight substance which is used in a photographic emulsion, a surface active agent is advantageously used. Particularly, an anionic surface active agent such as sodium cetylsulfate, sodium p-dodecylbenzenesulfonate, sodium nonylnaphthalenesulfonate, sodium di(2-ethylhexyl)-α-sulfosuccinate, etc., and a nonionic surface active agent such as sorbitan sesquioleate, sorbitan monolaurate, etc. are suitable. An emulsifying device such as a homogenizer, a colloid mill, an ultrasonic wave emulsifier, and the like is preferably used to prepare a dispersion of an oil-soluble coupler.

The diffusion resistant coupler which has both a ballasting group and a carboxylic acid group or a sulfonic acid group is soluble in a neutral or weakly alkaline aqueous solution. By addition of an aqueous solution of the coupler to a photographic emulsion, the coupler can be incorporated into the photographic emulsion. It is believed that the coupler is rendered diffusion resistant in a micellar form in the hydrophilic high molecular weight substance.

The so-called coupler-in-the-developer type couplers which are not diffusion resistant are used by addition to a color developer solution containing an aromatic primary amino color developing agent.

The silver halide photographic emulsions which can be used in the present invention include any known silver halide emulsion such as a silver bromide emulsion, a silver iodobromide emulsion, a silver chloroiodobromide emulsion, a silver chloride emulsion, and a silver chlorobromide emulsion or a silver halide emulsion of the so-called conversion halide type as described in, e.g., U.S. Pat. Nos. 2,592,250 and 3,622,318 and British Pat. No. 635,841. The silver halide grains can be of any size generally used in the photographic art but preferably have a grain size from about 0.02 to 5 microns, more preferably 0.1 to 2 microns.

Also, examples of the hydrophilic colloid which can be used for the coupler dispersion and the silver halide photographic emulsion are gelatin; a gelatin derivative such as acylated gelatin as described in U.S. Pat. No. 2,525,753, etc., graft gelatin as described in U.S. Pat. No. 2,831,767, etc., etc.; albumin; gum arabic; agar agar; a cellulose derivative such as acetyl cellulose, hydroxyethyl cellulose, carboxymethyl cellulose, etc.; and a synthetic resin such as polyvinyl alcohol, polyvinyl pyrrolidone, polyacrylamide, etc.

The silver halide emulsion can be chemically sensitized using active gelatin or a sulfur compound as described in U.S. Pat. Nos. 1,574,944; 1,623,499; 2,410,689; etc. Also, the emulsion can be sensitized using a salt of a noble metal such as palladium, gold, ruthenium, rhodium, platinum, etc., as described in U.S. Pat. Nos. 2,448,060; 2,399,083; 2,642,361; etc. Furthermore, the silver halide emulsion can be sensitized using a reducing agent such as a stannous salt, as described in U.S. Pat. No. 2,487,850, and also can be sensitized using a polyalkylene oxide derivative. Moreover, the silver halide emulsion can be spectrally sensitized with a cyanine dye or a merocyanine dye, as disclosed in U.S. Pat. Nos. 2,519,001; 2,666,761; 2,734,900; 2,739,964; 3,481,742; etc.

The silver halide emulsion can further contain a stabilizer such as a mercury compound, an azaindene, etc., as described in U.S. Pat. Nos. 2,886,437; 2,444,605; 2,403,927; 3,266,877; 3,397,987; etc., a plasticizer such as glycerine as described in C. E. K. Mees and T. H. James *The Theory of Photographic Process*, page 55 – 54, the Macmillan Co., New York (1966), and U.S. Pat. Nos. 2,904,434; 2,940,854; etc.

The photographic light-sensitive material of the present invention comprises a support having thereon at least one emulsion layer containing the coupler of the present invention.

As the support, examples are a cellulose ester film such as a cellulose nitrate film, a cellulose acetate film, etc.; a polyester film such as a polyethylene terephthalate film, etc., a polyvinyl chloride film, a polystyrene film, a polycarbonate film, a paper, a so-called baryta-coated paper prepared by coating barium sulfate on a paper support, a laminate film prepared by coating a cellulose ester, a polyester, a polyvinyl chloride, a polystyrene, or a polycarbonate on a paper or a baryta-coated paper, and a synthetic paper. A suitable coating amount of the silver halide can range from about $4 \times 10^{-4}$ to $4 \times 10^{-2}$, preferably $2 \times 10^{-3}$ to $2 \times 10^{-2}$, mol/m$^2$.

The photographic material of the present invention can have, in addition to the above-described silver halide emulsion layers, other layers conventionally employed for constituting the color photograhic material, such as, for instance, a protective layer, a filter layer, an intermediate layer, an antihalation layer, a subbing layer, a backing layer, a layer containing an ultraviolet absorber, etc. Also, as the binders for these layers, the hydrophilic colloid used for the silver halide emulsion layers can be employed.

Each layer of the color photographic material of the present invention can contain a hardening agent for the hydrophilic colloid. Typical examples of such hardening agents are aldehyde type compounds such as formaldehyde, glyoxal, succinaldehyde, glutaraldehyde, 2,3-dihydroxy-1,4-dioxane, mucochloric acid, dimethylolurea, etc.; active vinylic compounds such as divinylsulfone, methylene bismaleimide, 5-acetyl-1,3-diacryloyl-1,3,5-hexahydrotriazine, N,N',N'-triacryloyl-1,3,5-hexahydrotriazine, etc.; active halogen compounds such as 2,4-dichloro-6-oxytriazine sodium salt, 2,4-dichloro-6-methoxytriazine, sebacic acid bis-chloromethyl ester, N,N'-bis($\alpha$-chloroethylcarbamyl)-piperazine, etc.; epoxy compounds such as bis(2,3-epoxypropyl)methylpropyl ammonium para-toluene sulfonate, 1,4-bis(2',3'-epoxypropyloxy) butane; 1,3-diglycidyl-5-($\gamma$-acetoxy-$\beta$-oxypropyl)isocyanurate, etc.; ethyleneiminic compounds such as 2,4,6-triethyleneimino-1,3,5-trazine, bis-$\beta$-ethylene-iminoethyl thioether, etc.; and methane sulfonate compounds such as 1,2-di(methanesulfonyloxy) ethane, 1,4-di(methanesulfonyloxy)butane, 1,5-di(methanesulfonyloxy)-pentane, etc., as described in U.S. Pat. Nos. 3,232,764; 3,288,775; 2,732,303; 3,635,718; 3,232,763; 2,732,316; 2,586,168; 3,103,437; 3,017,280; 2,783,611; 2,725,294; 2,725,295; 3,100,704; 2,091,537; 3,321,313; etc.

Further each layer of the photographic material can contain a coating aid such as saponin, polyethylene glycol monolauryl ether, etc., as described in U.S. Pat. Nos. 3,415,649; 3,441,413; 3,502,473; 3,514,293; 3,506,449; 3,539,352; 3,545,974; 3,507,660; 3,442,654; 3,475,174; 3,462,520; 3,493,379; 3,516,833; 3,516,835; 3,589,906; 3,617,292; 3,619,199; 3,663,229; 3,666,478; etc., an antistatic agent as described in U.S. Pat. Nos. 2,739,888; 3,428,456; 3,437,484; 3,457,076; 3,549,375; 3,549,369; 3,551,152; 3,552,972; 3,547,643; 3,564,043; 3,615,531; 3,625,695; 3,655,287; 3,653,806; 3,655,386; 3,686,368; 3,756,828; 3,754,924; etc., an ultraviolet absorber as described in U.S. Pat. Nos. 3,415,624; 3,052,636; 3,074,971; 3,085,097; 3,067,456; 3,215,536; 2,719,086; 2,537,877; 2,784,087; 2,882,150; 2,875,053; 2,739,971; 3,097,100; 3,060,029; 2,632,701; 2,858,346; 2,748,021; etc., a fluorescent whitening agent as described in U.S. Pat. Nos. 3,630,738; 3,615,544; 3,586,673; 3,434,837; British Pat. Nos. 1,332,475; 1,319,763; 1,333,586; etc., an anti-irradiation dye as disclosed in U.S. Pat. No. 3,445,231, etc.

In the color photographic material containing the coupler or couplers of the present invention, any couplers other than the coupler of the present invention can also used. For instance, as a yellow dye-forming coupler there are the open chained type ketomethylenic couplers and typical examples of such couplers are benzoylacetanilide couplers, acylacetanilide couplers, etc. As a magenta dye-forming coupler, there are pyrazolone type couplers, indazolone type couplers, pyrazolobenzimidazole type couplers, cyanoacetyl type couplers, etc. Also, as cyan dyeforming couplers, there are illustrated phenol type couplers, naphthol type couplers, etc. Suitable examples of these couplers which can be used are described in U.S. Pat. Nos. 1,108,028; 2,186,849; 2,206,142; 2,343,702; 2,367,531; 2,369,489; 2,483,730; 2,436,130; 2,473,293; 2,600,788; 2,689,793; 2,728,658; 2,742,832; 2,808,329; 2,998,314; 3,046,129; 3,062,653; 3,265,506; 3,311,476; 3,408,194; 3,419,390; 3,419,391; 3,458,315; 3,476,563;

3,516,831; 3,617,291; 3,551,155; 3,551,156; 2,908,573; 3,642,485; 3,062,653; 3,558,319; etc.

Each of these couplers can have at the active carbon of the coupling position a group capable of being released on oxidative coupling with an aromatic primary amine developing agent, such as a halogen atom, an ether, thioether, a cyloxy, phthalimido, hydantoin, thiocyano, sulfo, sulfino, saccharin, benzotriazole, etc., group, besides a hydrogen atom. Also, the coupler can be a so-called colored coupler having a chromophore such as a diazo group, a styryl group, etc., as a releasable group. Furthermore, the coupler can have a so-called diffusion resistant group so that the coupler is prevented from diffusing in the emulsion layers. Also, the coupler can have a group such as a sulfo group, a carboxyl group, etc., for dispersing the coupler in a micellar state as an alkali metal salt or an alkaline earth metal salt thereof.

The emulsion containing the yellow color forming coupler of the present invention can constitute at least one photographic emulsion layer of a conventional multilayer silver halide color photographic material comprising a support having thereon a blue-sensitive silver halide emulsion layer containing a yellow dye-forming coupler, a green-sensitive emulsion layer containing a magenta dye-forming coupler, and a red-sensitive emulsion layer containing a cyan dye-forming coupler. The silver halide emulsion can also be appropriately used in multilayer materials such as those disclosed in U.S. Pat. Nos. 3,582,322; 3,622,318; 3,547,640; 3,672,898; 3,516,831; 3,705,799 – 3,715,208; 3,737,312; 3,703,375; 3,379,529; 3,402,046; 3,620,747; and 3,450,536; British Pat. No. 923,045; U.S. patent application Ser. No. 206,060, filed Dec. 8, 1971 and Ser. No. 29,666, filed Apr. 17, 1970.

The color photographic material containing the coupler of the present invention can be processed, after exposure, using known processing methods. For instance, when the photographic material of this invention is a negative-positive type negative or positive color photographic material, the color photographic material can be processed using the following main steps:

1. Color development
2. Stop or fix
3. Bleach and fix, or blix

Of these steps the second step can be omitted. Also, if desired, a hardening step for hardening the emulsion layers and an alkaline bath pre-treatment step for removing a resin backing layer can be employed before the first step, or step 1 described above. Furthermore, if desired, a hardening step can be employed between step 1 and step 2 or step 2 and step 3 or further after step 3. Still further, if desired, a stabilization step for improving the stability of images formed can be employed. Moreover, washing steps can also be employed between each step and after the last step.

After all of the photographic process steps are finished, the color photographic material is dried. That is to say, the color photographic material can be dried by natural drying by exposure to air, heating, hot-air drying, infrared radiation, electron rays, etc.

When the color photographic material containing the coupler of the present invention is used as a reversal type photographic material, the color photographic material is processed using the following main steps:

1. Black and white development
2. Reversal exposure
3. Color development
4. Stop or fix
5. Bleach and fix or blix When the bath for color development step 3 contains a fixing agent, step 2 can be omitted. In reversal processing, a hardening step, an alkaline bath pre-treatment step, a stabilization step, and washing steps can be, if desired, employed before or after each step described above. Also, after finishing all of the processing steps, the color photographic material is also dried as described for the aforesaid negative-positive type treatment.

For each step of the aforesaid negative-positive type treatment and the reversal type treatment, processing baths of known compositions can be used.

A useful color developer is an alkaline solution containing a color developing agent. As the color developing agent, any known aromatic primary amine developing agents can be used as disclosed, for example, in U.S. Pat. Nos. 2,592,364; 2,193,015 and C. E. K. Mees, T. H. James, *The Theory of the Photographic Process*, pages 294 – 295, Macmillan Co., (1966), such as N,N-diethyl-p-phenylene diamine, N-ethyl-N-hydroxyethyl-p-phenylene diamine, N-ethyl-N-hydroxyethyl-2-methyl-p-phenylene diamine, N-ethyl-N-$\beta$-methanesulfonamidoethyl-3-methyl-4-aminoaniline, N,N-diethyl-2-methyl-p-phenylene diamine, and the sulfates, hydrochlorides, sulfites of these compounds.

The color developer used for developing the color photographic material of this invention can further contain conventional additives such as an alkali metal (e.g., sodium or potassium) sulfite, an alkali metal carbonate, an alkali metal bisulfate, an alkali metal bromide, an alkali metal iodide, benzyl alcohol, a water softener (such as sodium hexametaphosphate, an alkali metal hydroxide, hydroxylamine, a sulfate of hydroxylamine, and a hydrochloride of hydroxylamine), a competitive coupler (such as mono-sodium 1-amino-8-naphthol-3,6-disulfonate, citrazinic acid, etc.), and the like.

In addition, as described above, the color developer can contain the coupler of this invention. A suitable amount of the coupler ranges from about 0.5 to 10 g, preferably 1 to 5 g, per liter of the color developer.

The stop solution used in the aforesaid processings can contain a known pH-reducing agent (such as acetic acid, phthalic acid, etc.).

The fix solution can contain a known fixing agent such as sodium thiosulfate, ammonium thiosulfate, potassium thiocyanate, etc.

The bleach solution can contain a known bleaching agent such as a ferricyanide (e.g., potassium ferricyanide), a bichromate (e.g., potassium bichromate), a ferric salt of ethylenediamine tetraacetic acid, etc.

When the bleach step and the fix step are conducted in one bath, a blix bath containing a known solvent for silver halide and a known silver oxidizing agent can be used. Examples of such a silver halide solvent are a thiosulfate (e.g., ammonium or potassium thiosulfate), a thiocyanate (e.g., ammonium or potassium thiocyanate), an organic diol containing an oxygen or sulfur atom (such as 3-thio-1,5-pentanediol, 3,6-dithio-1,8-octanediol, 9-oxo-3,6,12,15-tetrathia-1,17-heptadecanediol, etc.), a sulfur-containing organic dibasic acid or a salt thereof (such as ethylenebisthioglycolic acid, a sodium salt thereof, etc.), imidazolidinethione, and the like. Also, examples of the oxidizing agent for silver are a ferricyanide (e.g., potassium or ammonium ferricyanide), a quinone (e.g., quinone, p-benzoquinone, o-benzoquinone, p-toluquinone, 1,2-naphthoquinone), a ferric salt (e.g., a chloride or sulfate), a cupric salt (e.g., a chloride or sulfate), a cobaltic acid or salt (e.g., a chloride or sulfate) a complex salt of an ammonium ion or alkali metal ion, a ferric ion, a cupric ion, or a cobalt ion, and an organic acid (such as malonic acid, tartaric acid, ethylmalonic acid, malic acid, fumaric acid, diglycolic acid, dithioglycolic acid, ethyliminopropionic acid, nitrilotriacetic acid, ethylenediamine tetraacetic acid, aminotriacetic acid, ethylenedithioglycolic acid, dithioglycolic acid, etc.), and a chelate compound of a ferric ion, a cupric ion, or a cobalt ion (examples of coordination compounds of these chelate compounds are ethylenediamine, diethylenetriamine, triethylenetetramine, diaminopropane, diaminocyclohexane, polyethyleneimine, acetylacetone, diethyldithiocarbamate, oxyquinoline, dithizone, dipyridyl, phenanthrenine, etc., ferric ethylenediaminetetraacetic acid sodium salt, cupric malonic acid sodium salt), and the like.

These photographic processing compositions, and the components and proportions contained therein are well known in the art, as disclosed in *The Journal of the Society of Motion Picture and Television Engineers*, Vol. 61, page 667 – 701; U.S. Pat. Nos. 3,189,452 and 3,582,322; L. F. A. Mason, *Photographic Processing Chemistry*, page 187 – 188, Focal Press (1966), German Pat. No. 866,605 and 966,410; and the *British Journal of Photography*, page 122 – 123, 126 (1966).

The couplers of the present invention can be used, in addition to the aforesaid color photographic materials based on the subtractive color process, for other silver halide photographic materials forming color images by color development using aromatic primary amino developing agents, such as color radiographic photographic materials, infrared photographic materials, photographic materials for radar images, color microphotographic materials, and the like.

The yellow color forming couplers which can be used in the present invention comprise couplers in which one hydrogen atom attached to the carbon atom of the α-position in α-acylacetamides is substituted with a 5-alkylidene-3-hydatoinyl group.

The couplers which can be used in the present invention have the valuable features as shown below.

The α-imido-α-acylacetamide type couplers of the present invention are 2-equivalent couplers, and they require only two equivalents of silver halide as an oxidizing agent for forming one molecule of dye. These couplers require only half the amount of silver halide in comparison with 4-equivalent acylacetamide type couplers which have been widely used, and thus the amount of silver halide added to a photographic light-sensitive material can be reduced resulting in a decrease in the cost of production of the photographic light-sensitive material, an improvement of image sharpness due to a decrease in light scattering in the emulsion layer, and in addition a decrease in processing time of photographic light-sensitive material due to a decrease in the thickness of the emulsion layer.

The imido type couplers which can be used in the present invention have a high coupling reactivity to the oxidation products of a primary aromatic amino color developing agent, and thus they can rapidly react with the oxidation products of the color developing agent formed upon color development to facilitate the development of the silver halide emulsion. As a consequence the dye image formation of the present invention can be carried out in a short period of time. Also, since the couplers have a high coupling reactivity, a sufficiently high color density can be obtained when an amount of the solvent which is used to disperse the oil-soluble coupler, particularly nonvolatile solvent, is markedly reduced. The decrease in the amount of the solvent which remains in the photographic light-sensitive material leads to an increase in the mechanical strength of the emulsion layer.

The acylacetamide type couplers substituted with an imido group which can be used in the present invention can complete the dye formation step in the color developer solution and a bleaching bath containing a strong oxidizing agent such as potassium ferricyanide, potassium bichromate, etc. need not be used. They can be treated with a blix solution containing a weak oxidizing agent such as a ferric chelate of ethylenediamine-tetraacetic acid (EDTA) and a silver complex salt forming agent resulting in a shortened time of overall color processing and solving the problems of a water pollution due to waste from processing solutions. On the contrary, most acylacetamide type couplers in which the coupling site is not substituted do not complete the dye formation in the color developer solution and certain amounts of coupling reaction products remain in the leuco form which requires a strong oxidizing agent as described above to form the dyes completely.

The imido-substituted acylacetamide type couplers which can be used in the present invention provide dye images of extremely less tendency toward fading during storage under severe conditions for a long period of time.

According to the present invention, silver images which are simultaneously formed in the step of formation of dye images are easily oxidized in a bleaching bath or a blix bath and completely removed in a short processing time, and thus clear yellow dye images free from adverse affects due to remaining silver can be obtained.

The acylacetamide type couplers substituted with an imido group which can be used in the present invention can be prepared in high yield using raw materials which are industrially readily available.

The yellow color forming couplers which can be used in the present invention can be easily introduced and maintained stable in photographic materials.

The amount of the coupler which can be used in the present invention can be varied depending to the types of photographic light-sensitive material and developing process to which the coupler is subjected. In the case of the incorporated couplers, they can be preferably used in a range of about 0.02 to about 1.0 moles per mole of silver halide in the emulsion layer. If the amount incorporated is excessively less than about 0.02 moles per mole of silver halide a large amount of silver halide is required to give the desired color density, and thus the thickness of the emulsion layer tends to increase, which results in an increase in the light scattering in the silver halide emulsion layer reducing the sharpness of the images produced. Also the increase in the thickness of the emulsion layer results in an increase in the time required for processing and inhibits rapid processing. On the other hand, if the amount of coupler incorporated is excessively greater than about 1.0 moles per mole of silver halide, the couplers which are not converted to dyes by color development remain in the emulsion layer and reduce the efficiency of coupler utilization. This is disadvantageous from an economical standpoint and results in an increase in the thickness of the emulsion layer accompanied by the above-described defects.

In the practice of the present invention, the yellow color forming couplers represented by the general formula (I) can be used alone or as a mixture thereof, or they can be used together with a coupler or couplers other than the couplers represented by the general formula (I).

The present invention will now be explained in greater detail by reference to the following examples, but the present invention is not intended to be interpreted as being limited to these examples.

EXAMPLE 1

A solution prepared by heating at 45° C a mixture of 63.0 g of the above-described Coupler (3), α-(4-methoxybenzoyl)-α-(5-α-bromo-n-propylidene-3-hydantoinyl)-2'-chloro-5'-[α(2,4-di-tert-amylphenoxy)butyramido]acetanilide, 60 ml of di-n-butyl phthalate and 120 ml of ethyl acetate was added to 600 ml of an aqueous solution containing 60 g of gelatin and 3.0 g of sodium p-dodecylbenzene sulfonate and stirred, then passed five times through a preheated colloid mill. Thus the coupler was finely dispersed in gelatin together with the solvent.

All of the coupler dispersion was added to 2 kg of a photographic emulsion containing 150 g of gelatin and 113.4 g silver iodobromide (iodide content 3 mole%), and then 21 ml of a 4% aqueous solution of 2-hydroxy-4,6-dichloro-s-triazine sodium salt was added as a hardener. After adjusting the pH to 6.5, the mixture was coated on a cellulose triacetate film in a dry thickness of 7.0 microns and a coated amount of the coupler of $2.0 \times 10^{-3}$ mole/m² to prepare a photographic light-sensitive material. This material was designated Sample A.

For comparison, a photographic light-sensitive material was prepared by carrying out the same procedure as described for Sample A except that 46.6 g of Coupler (a), 4-methoxybenzoyl-2'-chloro-5'-[α-(2,4-di-tert-amylphenoxy)butyramido]acetanilide, which had the same chemical structure as that of Coupler (3) but in which one of the hydrogen atoms of the active methylene group was not substituted, was used in place of Coupler (3), and the amounts of di-n-butyl phthalate and ethyl acetate were varied to 45 ml and 90 ml, respectively. This material was designated Sample B.

These photographic light-sensitive materials were subjected to stepwise exposure and processed in the following manner.

| Processing Step | Temperature (° C) | Time (minute) |
| --- | --- | --- |
| 1. Color Development | 20 | 12 |
| 2. Washing | 18 | 1 |
| 3. First Fixing | 20 | 4 |
| 4. Washing | 18 | 3 |
| 5. Bleaching | 20 | 5 |

-continued

| Processing Step | Temperature (° C) | Time (minute) |
| --- | --- | --- |
| 6. Washing | 18 | 3 |
| 7. Second Fixing | 20 | 3 |
| 8. Washing | 18 | 15 |

The composition of the color developer solution used was as follows:

| Color Developer Solution A | |
| --- | --- |
| Water | 1000 ml |
| Benzyl Alcohol | 12.0 ml |
| Sodium Hexametaphosphate | 2.0 g |
| Sodium Sulfite (anhydrous) | 2.0 g |
| Sodium Carbonate (monohydrate) | 27.5 g |
| Hydroxyamine Sulfate | 2.5 g |
| 4-Amino-3-methyl-N-ethyl-N-(β-methanesulfonamidoethyl) aniline Sesquisulfate (monohydrate) | 4.0 g |

The fixing solution used was an acidic aqueous solution containing sodium thiosulfate and sodium sulfite, and the bleaching solution used was a neutral aqueous solution containing potassium ferricyanide and potassium bromide.

After processing Sample A and Sample B, the transmission optical density to blue light was measured and the photographic properties obtained are shown in Table 1.

Table 1

| Sample | AgX/Coupler (mole ratio) | Fog | Sensitivity* | Gamma | Maximum Density |
| --- | --- | --- | --- | --- | --- |
| A | 8/1 | 0.12 | 100 | 1.82 | 2.45 |
| B | 8/1 | 0.08 | 96 | 1.56 | 2.23 |

*Relative value of exposure amount required to give a density of fog + 0.10

Referring to Sample A and Sample B, the maximum densities to blue light were measured which were obtained upon treatment for different periods of color development processing time. The results shown in Table 2 were obtained.

Table 2

| Sample | Coupler | Developing Time (minutes) | | | |
| --- | --- | --- | --- | --- | --- |
| | | 4 | 8 | 12 | 16 |
| A | (3) | 1.98 | 2.41 | 2.45 | 2.44 |
| B | (a) | 1.46 | 2.01 | 2.23 | 2.35 |

As shown by the above-described results, it can be understood that the coupler of the present invention is a superior coupler which provides a high sensitivity, latitude and maximum density.

EXAMPLE 2

A solution prepared by heating at 60° C a mixture of 34.7 g of the above-described Coupler (10), α-pivaloyl-α-(5-isopropylidene-3-hydantoinyl)-2'-chloro-5'-[α-(2,4-di-tert-amylphenoxy)butyramido]acetanilide, 35 ml of di-n-butyl phthalate and 70 ml of cyclohexanone was added to 400 ml of an aqueous solution containing 35 g of gelatin and 3.5 g of sodium dinonylnaphthalene sulfonate and stirred, then agitated vigorously in a high speed agitator for 30 minutes. The couplers were finely dispersed together with the solvents.

All of the coupler dispersion was added to 1 kg of a photographic emulsion containing 37.8 g of silver iodobromide (iodide content 2 mole%) and 75 g of gelatin, and then 30 ml of a 3% acetone solution of triethylene phosphoramide was added as a hardener. After adjusting the pH to 6.5, the mixture was coated on a paper, which had been resin-coated with polyethylene on both surfaces, in a dry thickness of 3.5 microns. On the coating a gelatin solution was coated in a dry thickness of 1.0 micron as a second layer. A green-sensitive silver halide emulsion layer containing a magenta color forming Coupler (b) of the structure shown below was then coated in a dry thickness of 3.5 microns as a third layer.

Coupler (b)

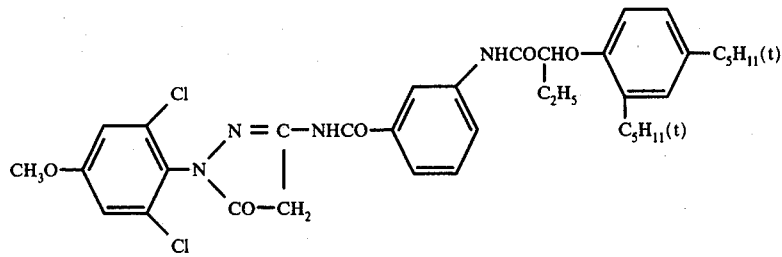

A gelatin solution containing 2-(2'-benzotriazolyl)-4,6-dibutylphenol as an ultraviolet absorbing agent was coated in a dry thickness of 2.5 microns as a fourth layer.

A red-sensitive silver halide emulsion layer containing a cyan color forming Coupler (c) of the structure shown below was coated in a dry thickness of 4.0 microns as a fifth layer.

Coupler (c)

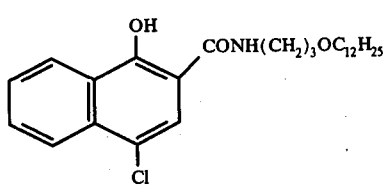

Further, a gelatin solution was coated in a dry thickness of 0.5 microns as an uppermost layer, thereby preparing a color printing paper.

The color printing paper was image-exposed through a color negative as an original and processed in the following manner.

| Processing Step | Temperature | Time |
|---|---|---|
| | (° C) | (minutes) |
| 1. Color Development | 24 | 6 |
| 2. Stop | 24 | 2 |
| 3. Blix | 24 | 6 |
| 4. Washing | 24 | 5 |

The color developer solution used was the same solution as used in Example 1, and the compositions of other processing solutions were as follows:

| Stop Solution | | |
|---|---|---|
| Water | 1000 | ml |
| Sodium Sulfite (anhydrous) | 5.0 | g |
| Glacial Acetic Acid | 15.0 | ml |
| Blix Solution | | |
| Water | 1000 | ml |
| Ammonium Thiosulfate | 105.0 | g |
| Sodium Sulfite (anhydrous) | 8.0 | g |
| Sodium Hydroxide | 18.0 | g |
| EDTA (disodium salt) | 35.0 | g |
| Ferric Chloride (hexahydrate) | 25.0 | g |
| Potassium Thiocyanate | 10.0 | g |

The color print thus obtained had a clear color and exhibited excellent color reproducibility. Particularly, a yellow color which was free from a reddish tint and had a good clearness and brightness was formed. The yellow dye image had an absorption maximum at 444 millimicrons.

The color print was exposed to a xenon arc lamp of 1.5 KW (about 15 × 10$^4$ lux) for 50 hours, and the density decreases for the yellow dye image were 0.05, 0.05 and 0.04 in areas of an initial density of 0.5, 1.0 and 1.5, respectively. Also the color print was stored under high temperature and high humidity conditions of 60° C, 75% RH for 2 weeks, and substantially no density decrease was observed.

EXAMPLE 3

A solution prepared by heating at 60° C on a steam bath a mixture of 22.5 g of the above-described Coupler (5), α-(4-methoxybenzoyl)-α-(5-α-bromo-n-propylidene-3-hydantoinyl)-2'-chloro-5'-[γ-2,4-di-tert-amylphenoxy)butyramido]acetanilide, 20 ml of tri-n-hexyl phosphate, 0.7 g of 2-tert-octyl hydroquinone and 40 ml of butyl acetate was added to 200 ml of an aqueous solution containing 1.0 g of sodium p-dodecylbenzene sulfonate and 20 g of gelatin and stirred, then passed five times through a preheated colloid mill.

All of the coupler dispersion was added to 500 g of a photographic emulsion containing 24.0 g of silver iodobromide (iodide content 3 mole%) and 37.5 g of gelatin, and then 6 ml of a 4% aqueous solution of 2-hydroxy-4,6-dichloro-s-triazine sodium salt was added as a hardener adjusting the pH to 6.0, a coating solution for a blue-sensitive emulsion layer was prepared.

On a polyethylene terephthalate film base, were coated, as a first layer, a gelatin solution containing black colloidal silver in a dry thickness of 2.5 microns for anti-halation; as a second layer, a red-sensitive silver halide emulsion containing a cyan color forming Coupler (d), 4,6-dichloro-5-methyl-2-[α-2,4-di-tert-amylphenoxy)acetamido]phenol in a dry thickness of 4.5 microns; as a third layer, a gelatin solution containing 2,5-di-tert-octylhydroquinone in a dry thickness of 1.5 microns; as a fourth layer, a green-sensitive silver halide emulsion layer containing the above-described magenta color forming Coupler (b) in a dry thickness of 4.5 microns; and as a fifth layer, a gelatin layer containing yellow colloidal silver in a dry thickness of 2.0 microns. On the fifth layer, were coated the above-described coating solution for the blue-sensitive emulsion layer in a dry thickness of 5.0 microns, and as an uppermost layer, a gelatin protective layer in a dry thickness of 1.0 micron, thereby preparing a color photographic film.

The film was exposed to light and subjected to the following processing.

| Processing Step | Temperature | Time |
|---|---|---|
| | (° C) | (minutes) |
| First Development (black and white) | 21 | 5 |
| Washing | 18 | 10 |
| Reversal Exposure | 18 | 1 |
| Second Development (color) | 21 | 12 |
| Stop | 21 | 2 |
| Blix | 21 | 8 |
| Washing | 18 | 10 |

In the first development a black and white developer of the following composition was used.

| First Developers Solution | | |
|---|---|---|
| Water | 1000 | ml |
| p-N-Methylaminophenol | 0.3 | g |
| Sodium Sulfite (anhydrous) | 38.0 | g |
| Sodium Carbonate (monohydrate) | 22.5 | g |
| Potassium Bromide | 0.9 | g |
| Citric Acid | 0.7 | g |
| Potassium Thiocyanate | 1.0 | g |

In the second development the color developer solution used in Example 1 was used, and in the blix, the blix solution used in Example 2 was used.

The reversal color photographic image thus obtained had a clear color and exhibited excellent color reproducibility.

EXAMPLE 4

A solution prepared by heating at 45° C a mixture of 28.5 g of the above-described Coupler (11), α-(4-methoxybenzoyl)-α-(5-isopropylidene-3-hydantoinyl)-2'-chloro-5'-[γ-(2,4-di-tert-amylphenoxy)-butyramido]acetanilide, 15 ml of di-n-butyl phthalate and 60 ml of cyclohexanone was added to 300 ml of an aqueous solution containing 30 g of gelatin and 1.5 g of sodium p-dodecylbenzene sulfonate and stirred, then agitated vigorously in a high speed agitator for 30 minutes. The couplers were finely dispersed together with the solvents.

All of the coupler dispersion was added to 1 kg of a photographic emulsion containing 75 g of gelatin and 56.7 g of silver iodobromide (iodide content 3 mole %), and then 30 ml of a 3% acetone solution of triethylene phosphoramide was added as a hardener. After adjusting the pH to 6.5, the mixture was coated on a cellulose triacetate film in a dry thickness of 7.0 microns and a coated amount of the coupler of $2.0 \times 10^{-3}$ mole/m$^2$ to prepare a photographic light-sensitive material. This material was designated Sample C.

For comparison, a photographic light-sensitive material was prepared by carrying out the same procedures as for Sample C except that 30.3 g of Coupler (e), α-(4-methoxybenzoyl)-α-(5-benzylidene-3-hydantoinyl)-2'-chloro-5'-[γ-(2,4-di-tert-amylphenoxy)-butyramido]acetanilide, which hs the same coupler residue but a coupling releasable group having a similar chemical structure to that of the coupling releasable group used in the coupler of the present invention, was used in place of Coupler (11). The material was designated Sample D.

These samples were subjected to stepwise exposure and processed in the following manner.

| | Processing Step | Temperature | Time |
|---|---|---|---|
| | | (° C) | (minutes) |
| 1. | Color Development | 20 | 15 |
| 2. | Washing | 18 | 1 |
| 3. | First Fixing | 20 | 4 |
| 4. | Washing | 18 | 3 |
| 5. | Bleaching | 20 | 5 |
| 6. | Washing | 18 | 3 |
| 7. | Second Fixing | 20 | 3 |
| 8. | Washing | 18 | 15 |

The composition of the color developer solution used was as follows:

| Color Developer Solution B | | |
|---|---|---|
| Water | 1000 | ml |
| 4-Amino-3-methyl-N,N-diethylaniline Hydrochloride | 2.5 | g |
| Sodium Sulfite (anhydrous) | 3.0 | g |
| Sodium Carbonate (monohydrate) | 47.0 | g |
| Potassium Bromide | 2.0 | g |

The fixing solution and the bleaching solution were the same solution as described in Example 1.

After processing Sample C and Sample D, the transmission optical density to blue light was measured and the photographic properties obtained are shown in Table 3.

Table 3

| Sample | Fog | Sensitivity* | Gamma | Maximum Density |
|---|---|---|---|---|
| C | 0.20 | 100 | 2.63 | 3.35 |
| D | 0.20 | 99 | 2.58 | 3.29 |

*Relative value of exposure amount required to give a density of fog + 0.10

Furthermore, the above-described coupler dispersion thus prepared was stored in a refrigerator at 5° C for 2 weeks and then added to the photographic emulsion and coated in the same manner as described above. The coating solution containing Coupler (11) of the present invention could be coated the same as the coupler dispersion just after the preparation thereof. On the contrary, the coating surface prepared using the coupler dispersion containing comparison Coupler (e) was not smooth and coupler deposition was observed. Also these samples were fixed without exposure and found that the transparency of Sample D was extremely low in comparison with that of Sample C.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive element which comprises a silver halide emulsion containing a yellow color forming coupler wherein said yellow color forming coupler has the general formula (I):

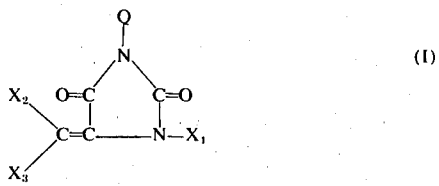

2. The light-sensitive element claimed in claim 1, wherein said alkyl group represented by $X_1$ is in the form of a chain and contains up to about 25 carbon atoms.

3. The light-sensitive element as claimed in claim 1, wherein said aryl group represented by $X_1$ is a phenyl group or a naphthyl group.

4. The light-sensitive element as claimed in claim 1, wherein said acyl group represented by $X_1$ has up to about 25 carbon atoms.

5. The light-sensitive element as claimed in claim 1, wherein said alkyl group represented by $X_2$ is in the form of a chain and contains up to about 25 carbon atoms.

6. The light-sensitive element as claimed in claim 1, wherein said alkyl group represented by $X_3$ is in the form of a chain and contains up to about 25 carbon atoms.

7. The light-sensitive element as claimed in claim 1, wherein said residue represented by Q is a residue of an α-acylacetamide coupler.

8. The light-sensitive element as claimed in claim 7, wherein said yellow color forming coupler has the general formula (II)

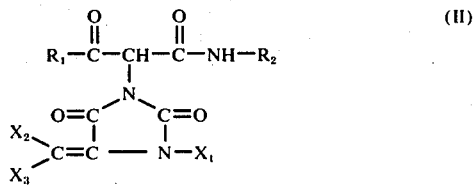

wherein $R_1$ represents an aliphatic group, an aromatic group or a heterocylic group; $R_2$ represents an aromatic group or a heterocyclic group; and $X_1$, $X_2$ and $X_3$ have the same meaning as defined in claim 8.

9. The light-sensitive element as claimed in claim 8, wherein said aliphatic group represented by $R_1$ is a tert-butyl group.

10. The light-sensitive element as claimed in claim 8, wherein said aromatic group represented by $R_1$ is a phenyl group or a phenyl group substituted with an electron-donating group.

11. The light-sensitive element as claimed in claim 8, wherein said aromatic group represented by $R_2$ is a phenyl group in which one of the ortho positions is substituted with a halogen atom, an alkyl group, an alkoxy group, or an N-substituted amino group.

12. The light-sensitive element as claimed in claim 8, wherein said yellow color forming coupler has the general formula (III):

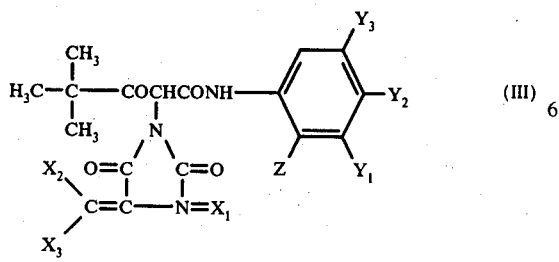

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, arylamino group, an acylamino group, a carboxy group, a sulfo group, a cyano group or a hydroxy group; and $X_1$, $X_2$ and $X_3$ have the same meaning as defined in claim 9.

13. The light-sensitive element as claimed in claim 8, wherein said yellow color forming coupler has the general formula (IV)

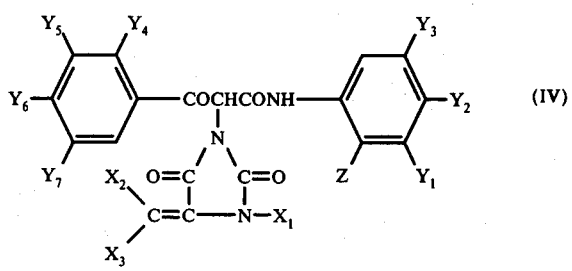

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; $Y_4$, $Y_5$, $Y_5$, and $Y_7$ each represents a hydrogen atom, an alkyl group, an alkoxy group, an aryloxy group, an amino group or an acylamino group; and $X_1$, $X_2$ and $X_3$ have the same meaning as defined in claim 9.

14. A photographic light-sensitive element comprising a support having thereon the color photographic light-sensitive element as claimed in claim 1.

15. A method of forming color photographic images which comprises developing an image-exposed color photographic silver halide emulsion layer with a primary aromatic amino color developing agent in the presence of a yellow color forming coupler, wherein said yellow color forming coupler has the general formula (I):

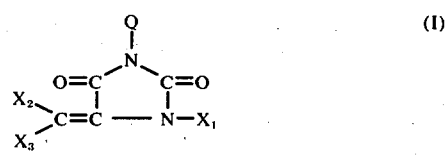

wherein $X_1$ represents a hydrogen atom, an alkyl group, an aryl group or an acyl group, $X_2$ and $X_3$ each represents a hydrogen atom, an alkyl group or a halogen atom, and Q represents a residue of an open-chain ketomethylene type yellow color forming coupler in which one hydrogen atom attached to the active methylene group of the coupler is eliminated.

16. The method of forming color photographic images as claimed in claim 15, wherein said alkyl group represented by $X_1$ is in the form of a chain and contains up to about 25 carbon atoms.

17. The method of forming color photographic images as claimed in claim 15, wherein said aryl group represented by $X_1$ is a phenyl group or a naphthyl group.

18. The method of forming color photographic images as claimed in claim 15, wherein said acyl group represented by $X_1$ has up to about 25 carbon atoms.

19. The method of forming color photographic images as claimed in claim 15, wherein said alkyl group represented by $X_2$ is in the form of a chain and contains up to about 25 carbon atoms.

20. The method of forming color photographic images as claimed in claim 15, wherein said alkyl group represented by $X_3$ is in the form of a chain and contains up to about 25 carbon atoms.

21. The method of forming color photographic images as claimed in claim 15, wherein said residue represented by Q is a residue of an α-acylacetamide.

22. The method of forming color photographic images as claimed in claim 21, wherein said yellow color forming coupler has the general formula (II)

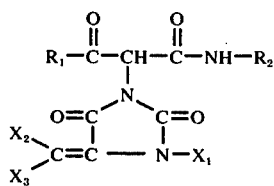

wherein $R_1$ represents an aliphatic group, an aromatic group or a heterocyclic group; $R_2$ represents an aromatic group or a heterocyclic group; and $X_1$, $X_2$ and $X_3$ have the same meaning as defined in claim 21.

23. The method of forming color photographic images as claimed in claim 22, wherein said aliphatic group represented by $R_1$ is a tert-butyl group.

24. The method of forming color photographic images as claimed in claim 22, wherein said aromatic group represented by $R_1$ is a phenyl group or a phenyl group substituted with an electron-donating group.

25. The method of forming color photographic images as claimed in claim 22, wherein said aromatic group represented by $R_2$ is a phenyl group in which one of the ortho positions is substituted with a halogen atom, an alkyl group, an alkoxy group, or an N-substituted amino group.

26. The method of forming color photographic images as claimed in claim 21, wherein said yellow color forming coupler has the general formula (III):

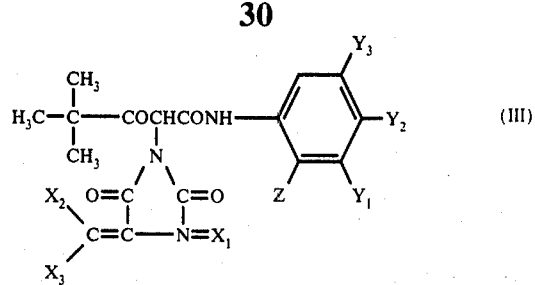

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, arylamino group, an acylamino group, a carboxy group, a sulfo group, a cyano group or a hydroxy group; and $X_1$, $X_2$ and $X_3$ have the same meaning as defined in claim 21.

27. The method of forming color photographic images as claimed in claim 21, wherein said yellow color forming coupler has the general formula (IV)

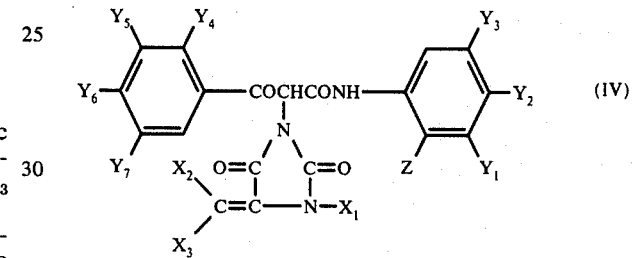

wherein Z represents a halogen atom, an alkyl group, an alkoxy group, an aryloxy group or an N-substituted amino group; $Y_1$, $Y_2$ and $Y_3$ each represents a hydrogen atom, a halogen atom, an alkyl group, an alkoxy group, an aryl group, an aryloxy group, an alkoxycarbonyl group, a carbamoyl group, a sulfamoyl group, an alkylamino group, an arylamino group, an acylamino group, a carboxy group, a sulfo group, a cyano group or a hydroxy group; $Y_4$, $Y_5$, $Y_6$, and $Y_7$ each represents a hydrogen atom, an alkyl group, an alkoxy group, an aryloxy group, an amino group or an acylamino group; and $X_1$, $X_2$ and $X_3$ have the same meaning as defined in claim 21.

* * * * *